US012778812B2

(12) United States Patent
Letchworth et al.

(10) Patent No.: US 12,778,812 B2
(45) Date of Patent: Nov. 3, 2026

(54) CUT-RESISTANT COMPRESSION SLEEVE

(71) Applicant: On Site Therapy, LLC, Tallahassee, FL (US)

(72) Inventors: Charles Letchworth, Tallahassee, FL (US); Robert Lisson, Tallahassee, FL (US)

( * ) Notice: Subject to any disclaimer, the term of this patent is extended or adjusted under 35 U.S.C. 154(b) by 0 days.

(21) Appl. No.: 18/940,712

(22) Filed: Nov. 7, 2024

(65) Prior Publication Data

US 2025/0248858 A1 Aug. 7, 2025

Related U.S. Application Data

(60) Provisional application No. 63/547,597, filed on Nov. 7, 2023.

(51) Int. Cl.
*A61F 13/10* (2006.01)

(52) U.S. Cl.
CPC .................................... *A61F 13/10* (2013.01)

(58) Field of Classification Search
CPC ........ A61F 13/085; A61F 13/00; A61F 13/10; A61H 1/008; A61H 9/005; A61H 2205/106; A41D 31/24; A41D 19/01505; A41D 13/088; A41D 31/245
See application file for complete search history.

(56) References Cited

U.S. PATENT DOCUMENTS

2006/0042327 A1* 3/2006 Hummel .................. D04B 1/14
66/202

* cited by examiner

*Primary Examiner* — Ophelia A Hawthorne
(74) *Attorney, Agent, or Firm* — Adrienne Love

(57) ABSTRACT

A cut-resistant compression sleeve for use on an arm of a user having a main body made up of a portion of fabric. Main body has an arm cuff, a wrist cuff and a hollow center. The portion of fabric is a weave including at least a cut-resistant material and an elastomeric material. The sleeve is capable of providing at least 13 mm Hg of compressive pressure and at most 18 mm Hg of compressive pressure inwardly on the arm of the user.

7 Claims, 7 Drawing Sheets

FULL ARM POWER Sleeves

| FULL ARM | Small | Medium | Large | X-Large | XX-Large |
|---|---|---|---|---|---|
| Wrist (A) | 5" - 6 1/4"<br>13 - 16 cm | 5 1/2" - 7"<br>14 - 18 cm | 6 1/4" - 7 3/4"<br>16 - 20 cm | 7" - 8 1/2"<br>18 - 22 cm | 8" - 9 3/4"<br>20 - 25 cm |
| Bicep (C) | 8 1/2" - 11 1/2"<br>22 - 30 cm | 10" - 13 1/4"<br>25 - 34 cm | 11 1/2" - 14 3/4"<br>30 - 38 cm | 13 1/4" - 16 1/4"<br>34 - 42 cm | 14 3/4" - 18 3/4"<br>38 - 48 cm |

FOREARM POWER Sleeves

| FOREARM | Small | Medium | Large | X-Large | XX-Large |
|---|---|---|---|---|---|
| Wrist (A) | 5" - 6 1/4"<br>13 - 16 cm | 5 1/2" - 7"<br>14 - 18 cm | 6 1/4" - 7 3/4"<br>16 - 20 cm | 7" - 8 1/2"<br>18 - 22 cm | 8" - 9 3/4"<br>21 - 25 cm |
| Forearm (B) | 6 1/2" - 8 1/2"<br>17 - 22 cm | 8" - 10"<br>20 - 25 cm | 9 1/4" - 11 1/2"<br>24 - 30 cm | 11 1/4" - 13 1/4"<br>29 - 34 cm | 12" - 14"<br>31 - 36 cm |

FIG. 7

CUT-RESISTANT COMPRESSION SLEEVE

CROSS-REFERENCES TO RELATED APPLICATIONS

Pursuant to the provisions of 37 C.F.R. § 119(e), this non-provisional application claims the benefit of an earlier-filed provisional patent application. The earlier application was assigned U.S. Ser. No. 63/547,597. It lists the same inventors.

STATEMENT REGARDING FEDERALLY SPONSORED RESEARCH OR DEVELOPMENT

Not Applicable

MICROFICHE APPENDIX

Not Applicable

FIELD

This invention relates to the field of devices made for applying compressive forces or pressure to a user's limb, such as the arm. More specifically, the invention comprises a compression sleeve that is cut-resistant and provides compression therapy when fitted to a user.

BACKGROUND

Traditional compression garments have been widely used to improve blood circulation in users, often to treat medical issues. These types of garments fit tightly around the body. Compression garments come in varying degrees of compression, where compression of 20-30 mmHg or higher typically require a doctor's prescription. The level of compression varies based on the size of the garment and the size of the user's body part covered by the garment.

Traditional compression sleeves are often designed with a medical patient in mind rather than a manual laborer or skilled tradesperson. Therefore, prior art garments fall short in terms of proper support, comfort, and performance for a user at work. Additionally, manual laborers or skilled tradesperson require the added protection of cut-resistance and comfort for use for an entire day. Therefore, what is needed is a garment that provides adequate comfort and compression for all day use in connection with repetitive work demands along with a garment that is cut-resistant. Further, it is important that the garment is sized appropriately to provide a desired amount of compression for peak performance and recovery for the user. The present invention achieves these objectives, as well as others that are explained in the following description.

SUMMARY

The cut-resistant compression sleeve includes a main body, wrist cuff, arm cuff and hollow cylindrical body. The fabric of the compression sleeve is made up of a cut-resistant material combined with sleeve materials, such as, for example, nylon, spandex, silicon and cotton. The interwoven resulting material provides flexibility, compressive force (13-18 mmHg), comfort (such as moisture wicking properties and softness), durability (ability to handle high temperature washing and drying and maintain appropriate size) and resistance to cuts. The sleeves are particularly beneficial to meet the demands of a worker who is engaged in repetitive movements throughout the day, such as pushing, pulling, lifting or repetitive gripping. These workers often are exposed to blades, sharp materials or other sharp edges. The sleeves act to significantly reduce fatigue, injury and soreness, along with the added benefit of reducing the risk of being cut during daily work activities. Additionally, many work industries require cut resistant personal protective equipment ("PPE")—the present compression sleeve will qualify as PPE for these types of industries.

The present compression sleeve comes in many sizes to ensure that each user can receive the correct size to achieve compression levels of 13-18 mmHg. The sleeve includes a very specific amount of gradient compression that is clinically proven to reduce cortisol lactate and aid with tendon health via microRNA. Additionally, a detailed description of the method of sizing the compression sleeves is provided herein. The sizing specifically ensures that proper compression is received by each individual user.

BRIEF DESCRIPTION OF THE DRAWINGS

FIG. 7 is a chart showing the present sizing measurements for the compression sleeve.

REFERENCE NUMERALS IN THE DRAWINGS

Figure 1:
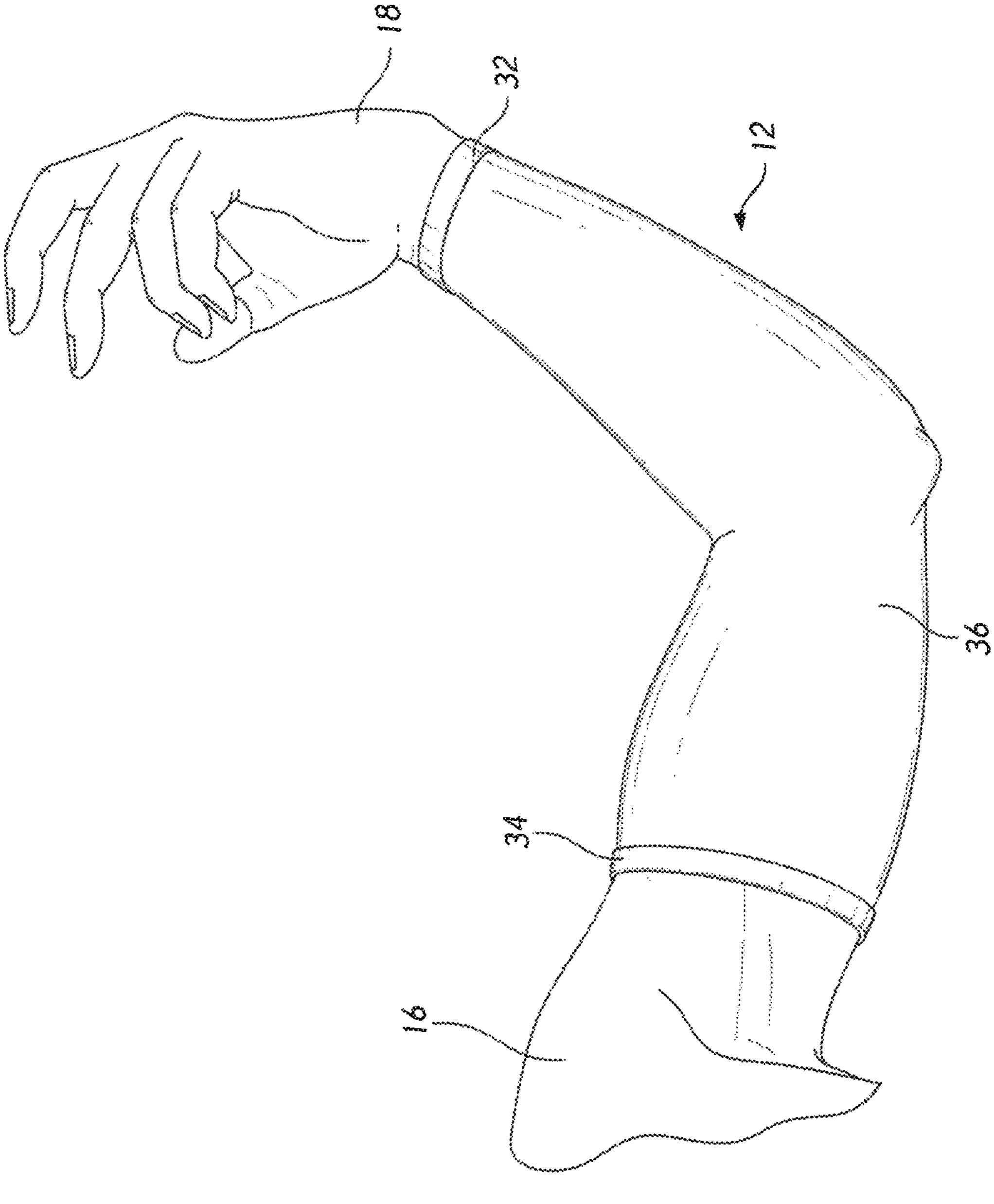
FIG. 1 is a perspective view, showing the full arm compression sleeve on the arm of a user.

10 user
12 full arm compression sleeve
14 forearm compression sleeve
16 upper arm of user
18 lower arm of user
20 tape measure
22 bicep measurement
24 elbow measurement
26 wrist measurement
28 fabric
30 blade
32 wrist cuff
34 arm cuff
36 main body
38 hollow interior
40 cut-resistant material
42 sleeve material
44 ground yarn
46 elastomeric inlay yarn
48 cut-resistant yarn

DETAILED DESCRIPTION

Figure 2:
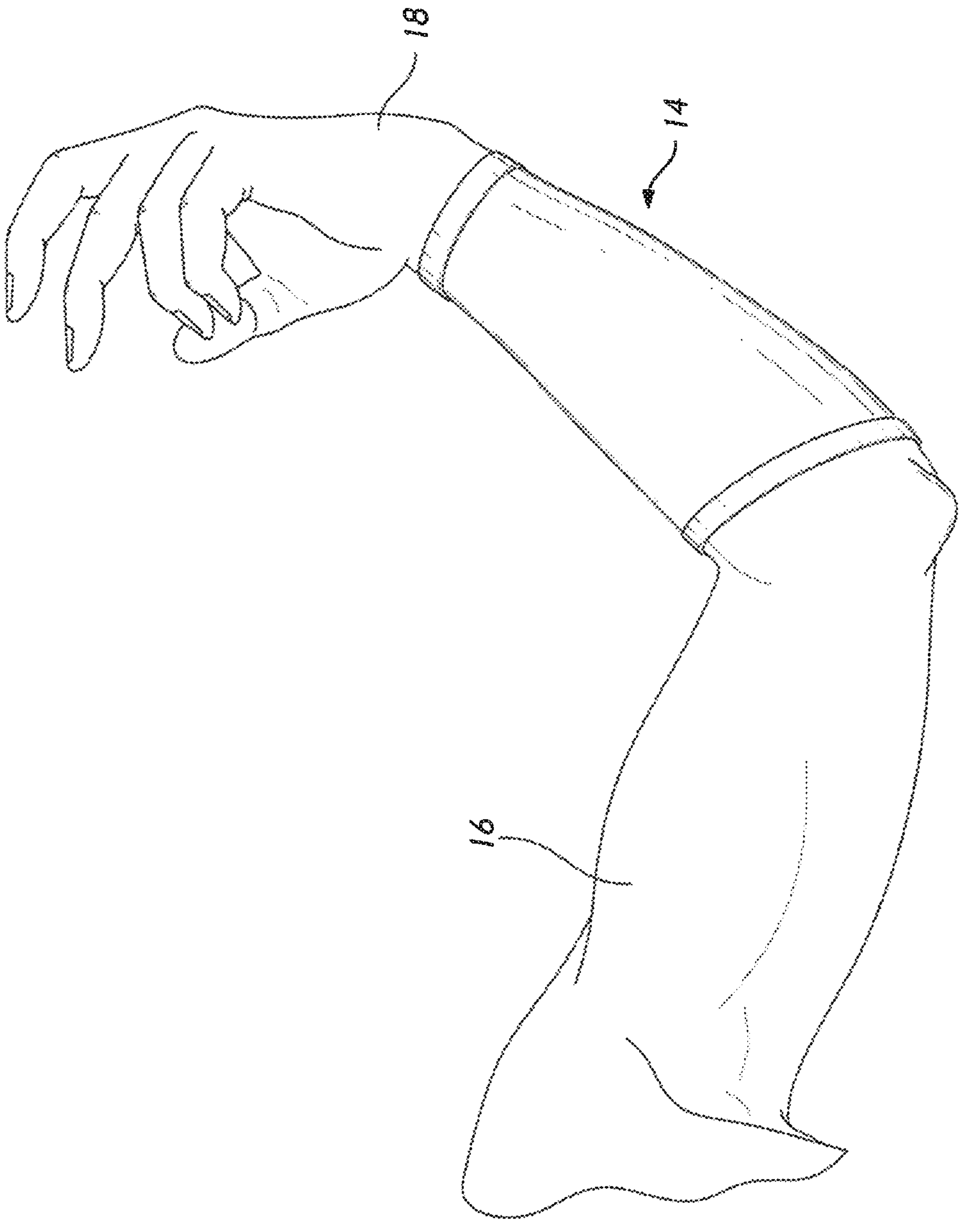
FIG. 2 is a perspective view, showing the forearm compression sleeve on the arm of a user.

FIG. 1 illustrates the present invention in full arm compression sleeve 12 embodiment. The user 10 has an upper arm 16 and a lower arm 18. Full arm compression sleeve 12 covers the user's arm from the wrist over the elbow to an area slightly below the armpit of the user. Full arm compression sleeve 12 has a main body 36, wrist cuff 32 at a first end, and an arm cuff 34 at a second end. Similarly, FIG. 2 shows the forearm compression sleeve 14, which includes a main body 36, wrist cuff 32 at a first end, and an arm cuff 34 at a second end. Forearm compression sleeve 14 covers the user's forearm from the wrist to a few inches below the elbow. Wrist cuff 32 of compression sleeve 12, 14 has a width and a terminal point (the end of the compression sleeve). Similarly, the arm cuff 34 of compression sleeve 12, 14 has a width and a terminal point (the end of the compression sleeve). Compression sleeve 12, 14 has an optional elastic loop to loop around the user's finger or thumb, or an optional strap that fits around the hand of the user to prevent the sleeve 12, 14 from sliding upward on the arm of the user. The optional loop or strap would attach to wrist cuff 32.

Compression sleeves 12, 14 offer variant gradient compression levels in the range of 13-18 mmHg. Gradient compression applies more pressure distally while gradually decreasing pressure as the sleeve travels up the arm. This encourages fluid movement. The specific level of compression provides fatigue management and a reduction of injuries for a user that engages in repetitive motions throughout their day, such as manual laborers or skilled tradesman. In order to ensure that the proper compression levels are provided to the arm of a user, the user must measure their arm to apply the appropriately sized sleeve.

Figure 3:
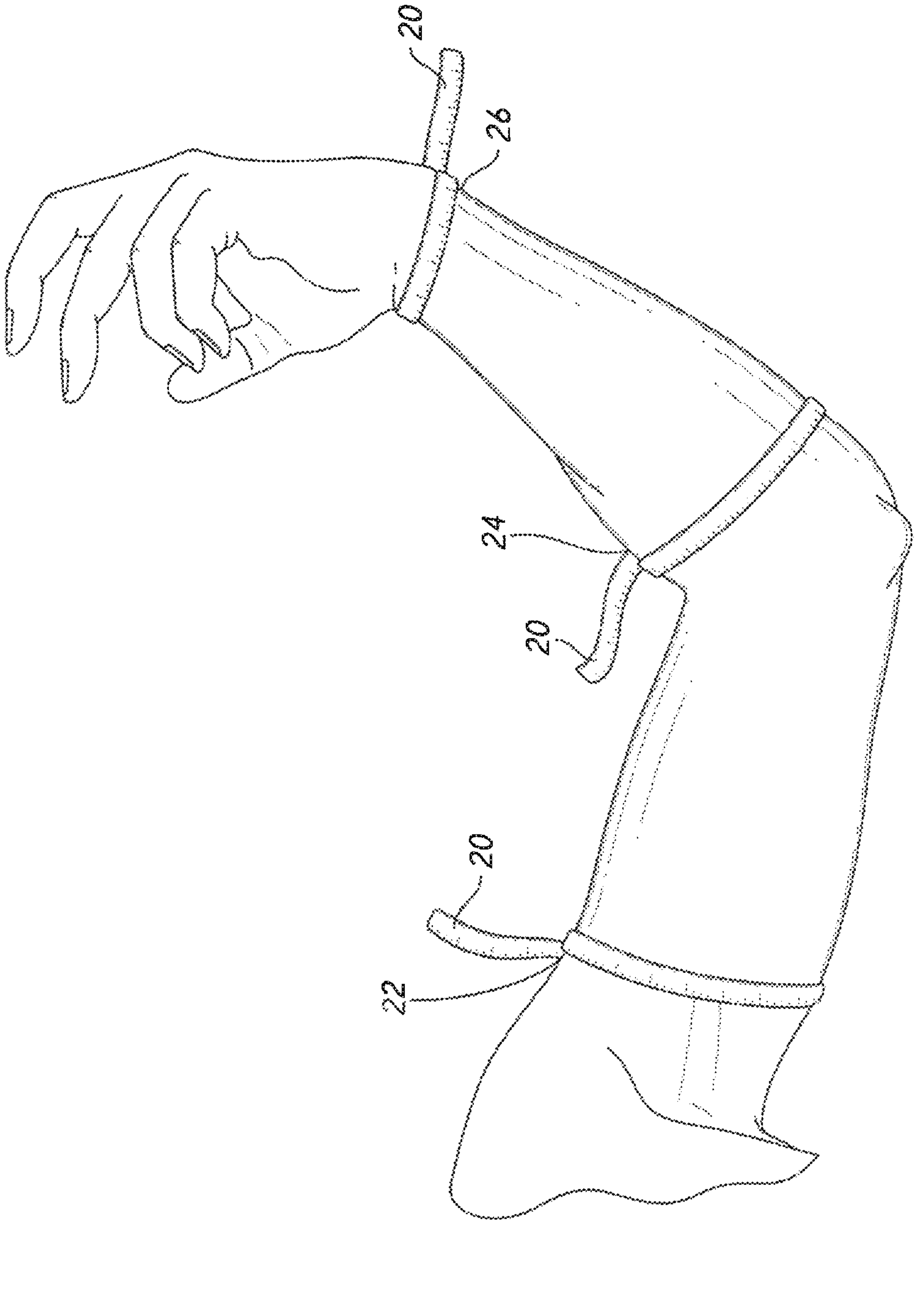
FIG. 3 is a perspective view, showing the points along the user's arm that must be measured to size the present compression sleeve.

An example of the method of selecting the present compression sleeve includes accurate measuring of the arm of the user. FIG. 3 illustrates the manner in which the arm is measured. The measurements are taken using a flexible tape measure (tailors tape) from points on the worker's dominant arm before the user performs substantial activity for the day. The measuring tape should be snug to the skin while ensuring a level angle of pull. Bicep measurement 22 is taken approximately two to three finger widths (or 3.2 to 6 cm) below the axillary crease (the skin crease in the armpit that marks the boundaries of the axilla). Elbow measurement 24 is taken one to two finger widths (or 1.6 to 4 cm) from the elbow crease and wrist measurement 26 is taken one to two finger widths (1.6 to 4 cm) from the base of the thumb (measurement is taken at the ulnar styloid bone and around the wrist). FIG. 7 shows the ideal measurements for each size of cut-resistant compression sleeve 12, 14. If the user meets two different size ranges, the larger size should be selected. As an example, if the user is selecting a full arm cut-resistant compression sleeve 12, 14 and has a wrist measurement that falls in the range of measurements for a small size, but has a bicep measurement that falls within the medium size range, the user should select the medium size. The sizing is carefully selected such that the user will receive the optimum level of compression (13-18 mmHg) against their arm at all times. Once the proper size is selected, the cut-resistant compressive sleeve 12, 14 is positioned on the arm of the user. The full arm cut-resistant compression sleeve 12 is positioned such that the wrist cuff is proximate the wrist of the user (where the wrist measurement was obtained, illustrated in FIG. 3) and the arm cuff is proximate the bicep of the user (where the bicep measurement was obtained, approximately two to three finger widths below axillary crease). The forearm compression sleeve 14 is positioned such that the wrist cuff is proximate the wrist of the user and the arm cuff is below the elbow of the user.

The performance of compression sleeves has been studied and proven. Compression sleeves 12, 14 are designed with physical work demands in mind. Often these demands require full arm movements that utilize the shoulder, arm, and forearm muscles when pulling, pushing, lifting or repetitive gripping. Specifically, as compared to not wearing compression sleeves, workers report that tightness, soreness, aching, fatigue and cramping was reduced by 80% or greater after wearing the present compression sleeve for a typical work day involving repetitive movements. Further, scientific testing has been performed on the present compression sleeves having the desired 13-18 mmHg compression. Studies found that the amount of cortisol and lactate build up in the muscle was greatly reduced by wearing 13-18 mmHg of compression versus no sleeves at all. This is important because cortisol and lactate contribute to or are correlated with muscle stress and injury. The results are reproduced in the table below.

TABLE 1

Values are shown from a female and male participant doing pre-exercise and post-exercise at 75-watts resistance on the cycle ergometer, followed by the collection of lactates, creatine kinase, and cortisol enzymes.

3. Results

| | Female no Sleeves | | Female w/ Sleeves | | Male no Sleeves | | Male w/ Sleeves | |
|---|---|---|---|---|---|---|---|---|
| | Pre | Post | Pre | Post | Pre | Post | Pre | Post |
| Creatine Kinase (ng/ml) | 9.43 | 9.02 | 4.63 | 5.00 | 8.61 | 4.59 | 6.79 | 6.21 |
| Cortisol (ng/ml) | 2807.67 | 2599.81 | 3768.47 | 2968.47 | 3492.91 | 3194.54 | 6951.72 | 4945.16 |
| Lactate (mmol/l) | 1 | 6.8 | 1.4 | 3.8 | 1.1 | 5.8 | 1.1 | 3.8 |

Wearing compression sleeves reduced by a factor of two the amount of muscle stress and muscle damage than not wearing compression sleeves. Values shown for the change in the creatine kinase were little to non-existent. However, measurements of lactate levels decreased significantly from pre to post exercise with and without sleeves.

The full arm compression sleeve 12 is designed with a relief stitch pattern over the elbow allowing increased freedom in performing these repetitive movements while maintaining the benefits of support and improved circulation. The compression sleeve 12, 14 is not only providing reduced fatigue markers and changes in lactate and cortisol levels after completion of work, but also provides safety from lacerations or larger cuts. The specific range of compression provided increase arterial blood flow, which reduces swelling and inflammation.

Figure 4:
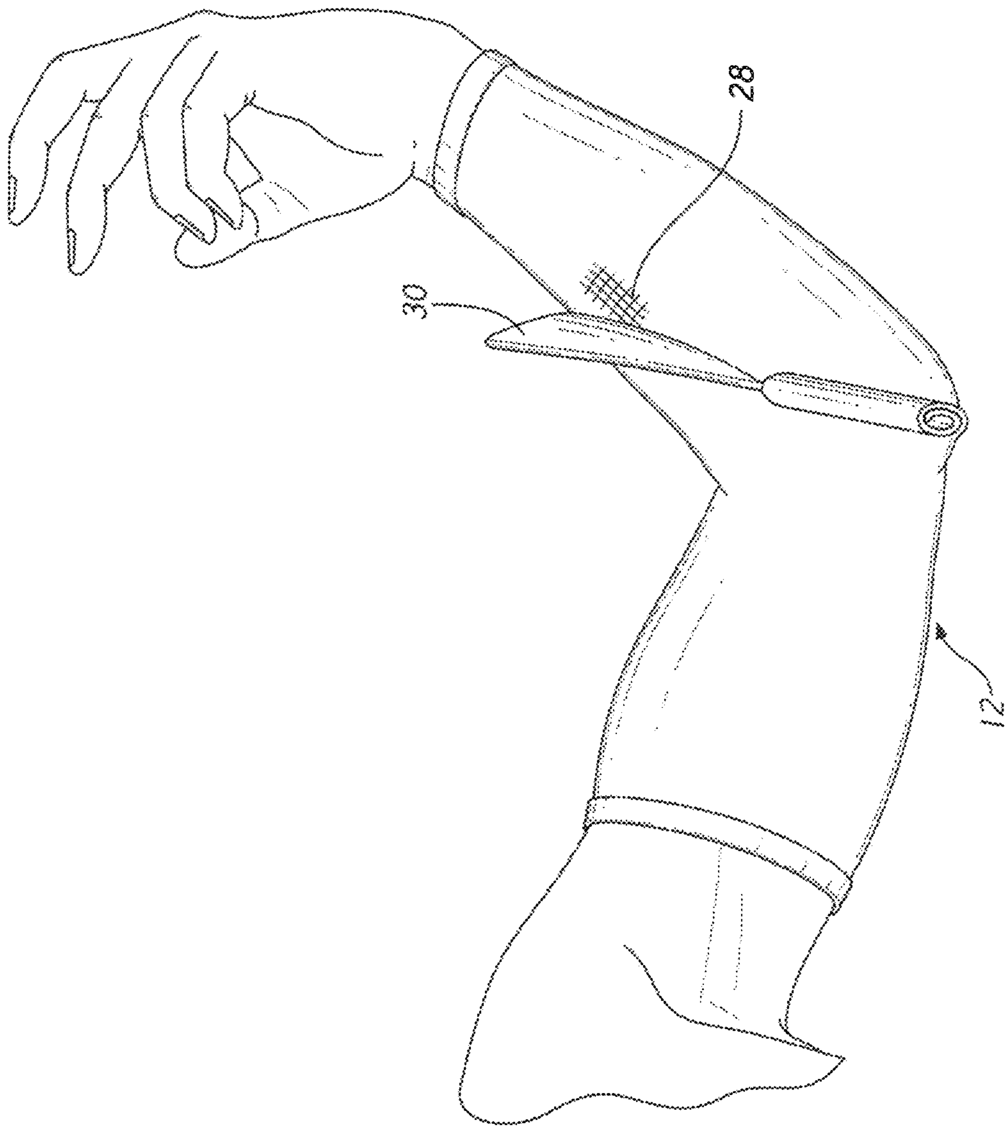
FIG. 4 is a perspective view, showing a blade contacting the present compression sleeve.
Figure 6:
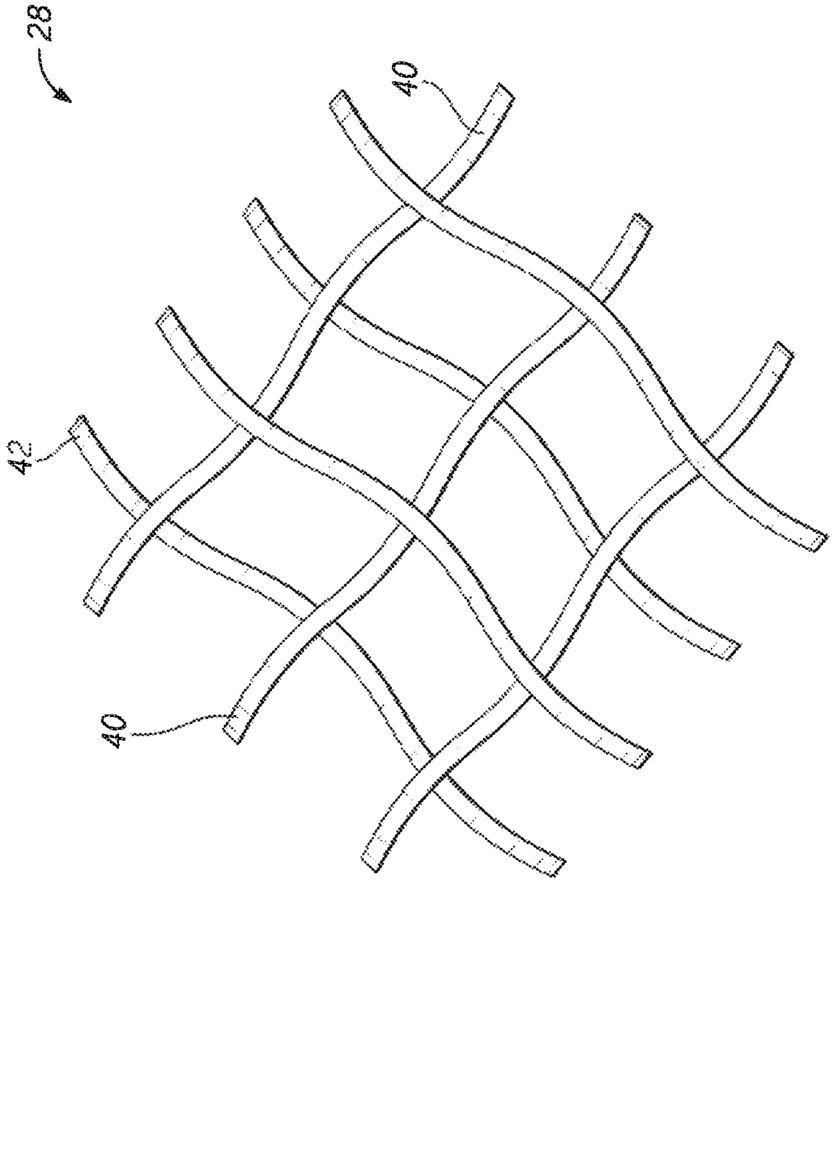
FIG. 6 is an exploded view, showing a portion of the fabric on the present compression sleeve.

Ultimately, the use of the compression sleeves 12, 14 in the work place is beneficial to the workers and the business. Further, the sleeves help reduce the potential for injury by incorporating a cut-resistant fabric woven or knitted into the compression sleeves 12, 14. As illustrated in FIG. 4, full arm compression sleeve 12 is shown on a user's arm. A knife blade 30 is shown contacting the sleeve 12. Full arm compression sleeve 12 protects the user from injury from the blade. The fabric 28 combines a cut-resistant material 40 interwoven or stitched into the sleeve material 42, as illustrated in FIG. 6. The reader will appreciate that FIG. 6 is a simplistic image of a woven material to create fabric, shown for purposes of illustrating the individual yarns in material. Any known method of weaving multiple materials together can be utilized. It is important that the cut-resistant material 40 combine with the sleeve materials 42 to provide the desired compression levels. Sleeve materials 42 can be any materials that provide flexibility while also providing adequate compressive force, comfort, moisture wicking and sturdiness. For example, nylon, spandex, silicon and cotton may be blended together to create the sleeve materials 42. It is also an object of this invention to provide fabric having the ability to be dyed to different colors. Each sleeve would be dyed according to their respective sizes. The color-coding of the sleeves will provide an ease in daily distribution of sizes to workers along with easy sorting of the sizes at the end of a shift.

Figure 5:
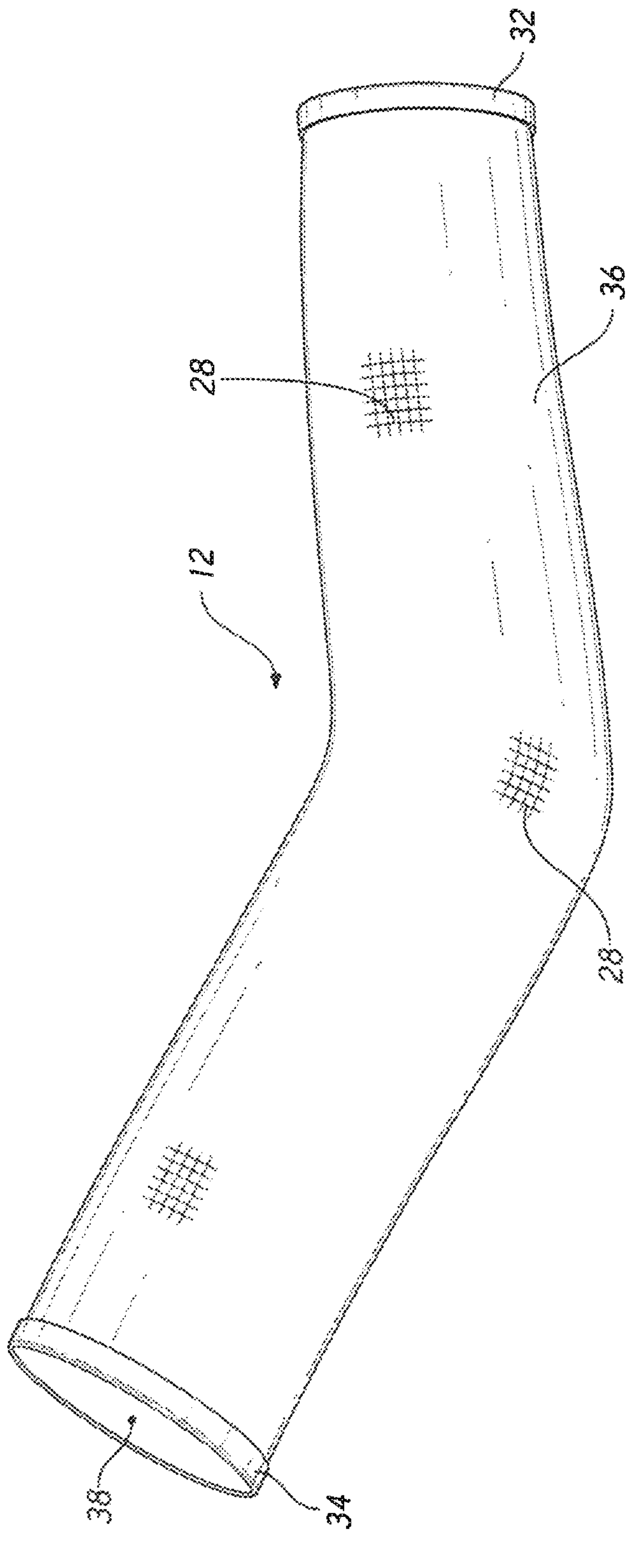
FIG. 5 is a perspective view, showing the full arm compression sleeve.

FIG. 5 shows full arm compression sleeve 12, including main body 36, wrist cuff 32, arm cuff 24, hollow body 38 and fabric 28. As discussed above, fabric 28 is cut resistant with compressive properties. The American National Standards Institute has defined levels of protection for cut resistant hand protection. The present compression sleeve 12, 14 will be designed to mirror those levels. For example, the currently defined levels include levels A1 through A9, each level includes a different cutting load. For example, level A1 protects against 200 to 499 g of cutting load, while level A9 protects against a minimum of 6000 g of cutting load. These levels correspond to certain industries. The meat processing industry requires level 7 or 8 protection. Fabric 28 of compression sleeve 12, 14 will be designed to meet the different levels of cut resistance as needed for the specific industry. Cut-resistant material 40 can be any material that is resistant to cuts. Typically, cut resistance is a function of the material composition and thickness. Some examples of cut-resistant material 40 (or fibers) include, but are not limited to, Spectra® Fiber (manufactured by Honeywell International, Inc., Charlotte, NC), Dyneema® (manufactured by DSM IP Assets B.V., Netherlands), Kevlar® Aramid Fiber (manufactured by DuPont Safety & Construction, Inc., Wilmington, Delaware) and Vectran® (manufactured by Kuraray Co., Ltd, Japan). Manufacturers use different tests to determine the cut protection performance of protective apparel. The performance of a particular fabric may be affected by the combination of the cut resistant material 40 and the sleeve materials 42. Returning to FIG. 6, the fabric 28 is comprised of these individual fibers (cut-resistant material 40 and sleeve material 42 that are woven together to create the compression sleeve. The fibers can be woven together in any known manner so long as maintaining the cut-resistance and desired compression levels of the sleeve 12, 14. Either a flat knit circular knit machine or seamless circular knit machine is used to manufacture the sleeve 12, 14. Compression sleeve fabric 28 could be made by knitting together at least three types of materials—the ground yarn (which ensures stiffness and thickness of the product), the elastomeric inlay-yarn (which generates required compression level) and the cut-resistant material 40 (which could, for example consist of aramid yarn). A knitted structure with a knitting pattern such as a combined laid-in jacquard or a plated rib 1×1 pattern can be utilized with elastomeric inlay-yarns and cut-resistant material 40 inserted into the weave. A plated rib 1×1 pattern can be used utilizing ground yarn, elastomeric inlay-yarn and cut-resistant yarn. As an example, an elastomeric inlay-yarn is inserted into every first, second and third course. The cut-resistant yarn is inserted into every fourth course. The fabric thereby retains its compressive characteristics while imparting cut resistance. This is one example of a knit pattern that could be used, however any number of patterns could be used so long as the sleeve 12, 14 retains the disclosed compression levels and achieves the desired cut-resistance tolerance.

The preceding description contains significant detail regarding the novel aspects of the present invention. It should not be construed, however, as limiting the scope of the invention but rather as providing illustrations of the preferred embodiments of the invention. Thus, the scope of the invention should be fixed by the claims, rather than by the examples given.

The invention claimed is:

1. A cut-resistant compression sleeve configured to be worn on an arm of a user, said arm having a wrist, a thumb and an elbow, comprising:

a main body with a wrist cuff at a first end and an arm cuff at a second end, wherein said main body has a hollow center and is made of a portion of fabric, wherein said arm cuff has an opening and said wrist cuff has an opening, wherein said main body is configured to receive said arm of said user through said hollow center, and wherein said fabric further comprises a weave made up of at least a series of ground yarns, a series of cut resistant yarns and a series of elastomeric inlay-yarns, and wherein said main body is configured to provides a compressive force in a range of at least 15 mm Hg and at most 18 mm Hg to said arm of said user when worn, and wherein said compressive force is a gradient compressive force within said range, configured to apply a greater amount of pressure distally while gradually decreasing pressure as said cut-resistant compression sleeve extends upward on said arm of said user when worn.

2. The cut-resistant compression sleeve of claim 1, wherein said portion of fabric is dyed to a color.

3. The cut-resistant compression sleeve of claim 2, wherein said color of said portion of fabric represents a specific size of said cut-resistant compression sleeve.

4. The cut-resistant compression sleeve of claim 1, wherein said wrist cuff further comprises an elastic loop to fit over said thumb of said user.

5. The cut-resistant compression sleeve of claim 1, wherein said main body has a relief stitch configured to be positioned over said elbow of said user when worn to allow increased freedom of movement.

6. The cut-resistant compression sleeve of claim 1, wherein an upper end of said arm cuff is configured to be positioned at least 3.2 cm to at most 6 cm below an axillary crease of said user when worn.

7. The cut-resistant compression sleeve of claim 1, wherein said arm cuff is configured to be positioned at least 1.6 cm to at most 4 cm below an elbow crease of said elbow when worn.

* * * * *